United States Patent [19]

Stock et al.

[11] Patent Number: 5,064,437
[45] Date of Patent: Nov. 12, 1991

[54] KNEE JOINT ENDOPROSTHESIS

[75] Inventors: Dietrich Stock, Braunschweig; Walter Hund, Oberkirch-Stadelhofen; Friemut Vizethum, Schwetzingen, all of Fed. Rep. of Germany

[73] Assignee: Friedrichsfeld AG Keramik- und Kunststoffwerke, Mannheim, Fed. Rep. of Germany

[21] Appl. No.: 653,239

[22] Filed: Feb. 11, 1991

[30] Foreign Application Priority Data

Feb. 16, 1990 [DE] Fed. Rep. of Germany ....... 4004787
Mar. 23, 1990 [DE] Fed. Rep. of Germany ....... 4009360

[51] Int. Cl.$^5$ ............................................. A61F 2/38
[52] U.S. Cl. ..................................................... 623/20
[58] Field of Search ......................................... 623/20

[56] References Cited

U.S. PATENT DOCUMENTS

| | | | |
|---|---|---|---|
| 4,016,606 | 4/1977 | Murray et al. | 3/1 |
| 4,085,466 | 4/1978 | Goodfellow et al. | 3/1.91 |
| 4,224,696 | 9/1980 | Murray et al. | 3/1.91 |

FOREIGN PATENT DOCUMENTS 3528204 2/1986 Fed. Rep. of Germany.
8717 12/1987 Fed. Rep. of Germany.

Primary Examiner—Randy Citrin Shay
Attorney, Agent, or Firm—Foley & Lardner

[57] ABSTRACT

A knee-jount endoprosthesis including a femoral part (2), a meniscus element (6) and a tibial part (12), the femoral part (2) and the tibial part (12) lying with their bearing surfaces in contact with associated bearing surfaces of the meniscus element (6). This endoprosthesis is capable of achieving the physiological knee-joint functions of movement and load-bearing while preventing local peak stresses, especially those caused by line or point contact. The femoral part (2) is provided with a spherical bearing surface (4) which lies on a corresponding spherical and concentrically disposed bearing surface (8) of the meniscus element (6). The tibial part (12) has a convex configuration and a cylindrical bearing surface which contacts a mating, coaxially arranged second bearing surface (10) on the meniscus element (6).

15 Claims, 3 Drawing Sheets

KNEE JOINT ENDOPROSTHESIS

BACKGROUND OF THE INVENTION

This invention relates to a knee-joint endoprosthesis comprising a femoral part, a meniscus element, and a tibial part, wherein the femoral part and the tibial part have bearing surfaces which contact associated bearing surfaces on the meniscus element.

U.S. Pat. No. 4,085,466 discloses a knee-joint endoprosthesis of this type, in which two artificial meniscus elements are disposed between spherically curved bearing surfaces on the femoral part and substantially planar bearing surfaces on the tibial part. The curved bearing surfaces of the femoral part and of the meniscus elements are expensive to produce, and due to production tolerances, it is hard to avoid localized high surface pressures per unit area. To facilitate some kind of equalization, the meniscus element is formed of flexible plastic. Slight departures from the geometry of the bearing surfaces and the resulting pressures per unit area and peak stresses can produce comparatively rapid wear and damage, substantially reducing the useful life of the prosthesis. It is known that, under compressive loading, plastics tend to develop permanent deformation, and the geometry of the originally complementary bearing surfaces changes. Making the meniscus elements from a flexible plastic, such as polyethylene for example, leads in practice to permanent deformation of the meniscus element after a period of time, so that the originally complementary configuration of the bearing surfaces of the femoral part and the meniscus element can no longer be assured, and the functionality of the endoprosthesis may be jeopardized. The meniscus element not only can execute linear movements on the planar bearing surface of the tibial part, but also can rotate about the axis which is perpendicular to the planar bearing surface of the tibial part and extends through the center of the spherically curved bearing surface of the femoral part. Therefore, additional abutments are provided to limit the angular range of rotation of the femoral part. This creates the danger that, due to linear or even point contact, high pressures per unit area, undesirably high peak stresses and damage may occur.

German Published Application No. DE 35 28 204 discloses a knee-joint endoprosthesis in which the femoral part and the tibial part each have a guiding means. These guiding means preferably take the form of a groove and projection cooperating with one another to enable flexional positioning in the sagittal plane. The guiding means are configured such that a mutual rotation between the femoral part and the tibial part is permitted in order thus to obtain an additional degree of freedom corresponding to the natural knee joint. Even in this knee-joint endoprosthesis the bearing surfaces of the femoral part are configured as spherically curved surfaces which in turn are mounted in contact with correspondingly curved surfaces of the tibial part. On the other hand, an additional meniscus element is not provided, so that the movements only roughly correspond to a natural knee joint.

U.S. Pat. No. 4,224,696 discloses an endoprosthesis having a tibial part with a curved bearing surface for the plastic meniscus element, the center of this curved bearing surface lies near the femoral part. The bearing surfaces of the femoral part and tibial part are substantially coaxial with one another and are configured to correspond approximately to the surface configurations of the natural parts of the knee joint. Only a single plastic meniscus element is provided having a convexly curved bearing surface in contact with the mating, concavely curved bearing surface of the single tibial part. The cost of manufacturing such a knee-joint endoprosthesis is considerable, and in practice it is impossible to avoid high pressures per unit area due to line contact.

SUMMARY OF THE INVENTION

It is the object of the invention to provide a knee-joint prosthesis which is capable of closely approximating the physiological knee joint functions of movement and load-bearing.

Another object is to provide a knee-joint prosthesis which transmits forces to large surface areas insofar as possible and avoids local peak stresses, especially due to line or point contact.

A further object of the invention is to provide a knee-joint prosthesis which has small dimensions.

An additional object of the invention is to provide a knee-joint prosthesis in which assures that the parts which move on one another have good tribological properties and that the force-transferring parts exhibit high static strength.

Yet another object of the invention is to provide a knee-joint prosthesis in which friction between the components moving on one another is minimized.

These and other objects of the invention are achieved by providing a knee-joint prosthesis comprising a femoral part, a meniscus element and a tibial part, wherein the femoral part and the tibial part have bearing surfaces which contact associated bearing surfaces on the meniscus element; the bearing surface of the femoral part has a spherical configuration and lies in contact with a spherically concave bearing surface of the meniscus element; the bearing surface of the tibial part has a convex cylindrical configuration and lies in contact with a coaxial, cylindrically concave bearing surface of the meniscus element, and the meniscus element is positively guided on the cylindrical bearing surface and secured against rotation about an axis extending through the center of the femoral part.

The proposed knee-joint endoprosthesis provides an optimal achievement of the physiological motions and static characteristics of the knee joint in a reliable and compact design. The bearing surface of the femoral part has a spherical configuration, while the bearing surface of the tibial part is cylindrical, and the associated bearing surfaces of the meniscus element are configured to match them spherically and cylindrically. In contrast to the condyles peculiar to the body, and their bearing surfaces of involute-like curvature, the two femoral parts have spherical bearing surfaces which can be manufactured with great precision, as can the corresponding concavely spherical bearing surfaces of the meniscus elements. The same also applies to the coaxial, cylindrical bearing surfaces of the tibial parts and the meniscus elements. The cylinder axes of the tibial parts, corresponding to the flexional axis, lie substantially parallel to a tibial plate on which the tibial parts are fixedly disposed. The axes of rotation of the convex cylindrical bearing surfaces of the tibial parts are situated close to the tibia, and in this manner a positive guidance of the meniscus element and the cylinder surface is assured, and the rotation mentioned above is reliably prevented. Abutments for preventing impermissible rotation of the biconcave meniscus elements about a vertical axis passing through the femoral part are not necessary. The combination of spherical bearing surfaces for the femoral part and cylindrical bearing surfaces for the tibial part, provides both surface control and positive guidance of the meniscus element on the cylinder surface in a desirable manner. Depending on the flexional position, a defined alignment of the meniscus element with respect to the tibial part and the femoral part is assured, and additional abutments, stops and the like are therefore unnecessary.

The axes of the two cylindrical surfaces of the tibial part can advantageously lie in a common plane which, when the tibial part and femoral part are in the extended position, also passes substantially through the centers of the two spherical bearing surfaces of the femoral parts. The two meniscus elements have a biconcave configuration, the bearing surface associated with the femoral part being spherical and the bearing surface associated with the tibial part being cylindrical. The meniscus element can, in an especially desirable manner, be made of a hard, deformation-free material, especially an oxide ceramic, thus assuring a long service life of many years for the endoprosthetic knee joint. This is in contrast to the previously known knee joint endoprosthesis whose meniscus elements were composed of a different synthetic material, namely a softer and more elastic one. The meniscus elements are desirably made from the same material as the femoral and tibial parts, using the biocompatible materials proven in implantation, particularly ceramics. As in the case of the natural knee joint, a lock against rotation occurs when the tibial part is extended from the femoral part, inasmuch as the two center points of the spherical bearing surfaces of the femoral parts lie in substantially the same plane as the cylinder axes of the bearing surfaces of the tibial parts. When the knee joint is flexed, the centers of the bearing surfaces shift toward the dorsal side and rotation then becomes possible. The meniscus elements can only move in two spatial directions with respect to the tibial part, namely they can rotate about the cylinder axis and undergo translation parallel to the cylinder axis. The cylinder surface, however, in this case prevents rotation about a vertical axis perpendicular to the tibial plateau. Also when the joint is extended again, the meniscus element is positively guided on the convex cylindrical bearing surface of the tibial part, and because of this positive guidance along the convexly curved bearing surface of the tibial part, the meniscus element reassumes its original position in the extended state.

To improve operation, the tibial bearing surfaces can, within the scope of this invention, also be tilted on one or both sides against the tibial plateau in order to improve the guidance and the biological adaptation. The two tibial parts disposed on the tibial plate can also have their cylinder axes inclined in the same direction or even in opposite directions with respect to the tibial plate, in which case the angles of inclination can be selected depending on the requirements of the situation. The angle or angles of inclination can range between 0 and ±45 degrees. A range between 0 and ±20 degrees has proven desirable. It is important that the meniscus element be movable radially and/or axially with respect to the cylindrical bearing surface of the tibial part. The femoral part, the bearing surfaces of the meniscus element and the tibial part make large surface area contact with one another regardless of the angle of rotation assumed by the femoral and tibial parts, while line contact and peak stresses are reliably prevented. The meniscus element can be made in an especially desirable manner of the same material as the femoral and tibial parts, and on the whole a high operational reliability and long service life are achieved. Lateral guidance of the meniscus element with respect to the tibial part in the direction of the cylinder axis can advantageously be omitted, thereby permitting equalization movements. The femoral part, meniscus element and tibial part are held together in an anatomically optimum manner by the intact kinematic apparatus with its ligaments and muscles, assuring an enduring surface-to-surface contact and reliably preventing line contact and overloading. The configuration of the joint surfaces of the tibia and femur furthermore permits the free, tissue-sparing mobility of the joint in accordance with the anatomical requirements.

BRIEF DESCRIPTION OF THE DRAWINGS

The invention will be described in further detail below with reference to illustrative embodiments depicted in the accompanying drawings in which.

DETAILED DESCRIPTION OF PREFERRED EMBODIMENTS

Figure 1:
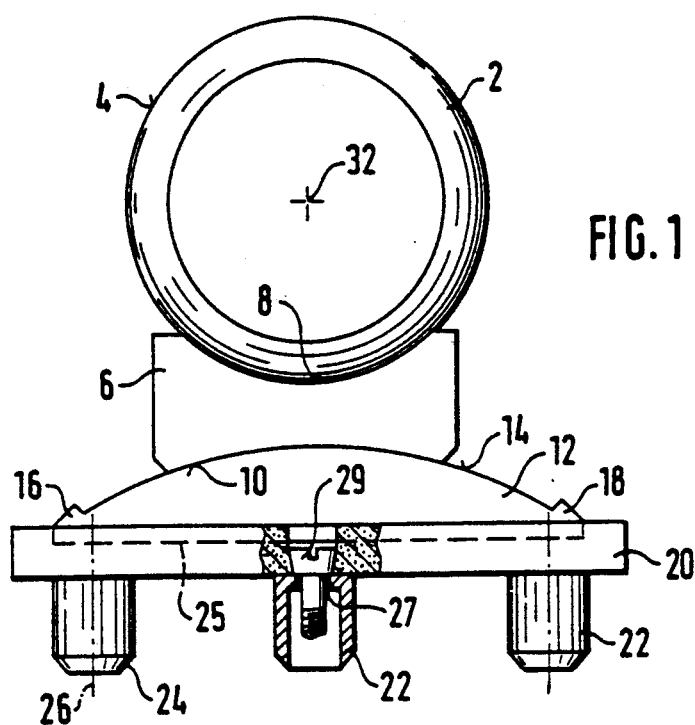
FIG. 1 is a schematic side elevational view.

FIG. 1 is a schematic side view of an endoprosthesis with a femoral part 2 having a spherical bearing surface 4. A meniscus element 6 has a correspondingly spherical first bearing surface 8. This first bearing surface 8 is concentric with the bearing surface 4 of the femoral part 2, and has the same radius. The biconcave meniscus element 6 also has a second bearing surface 10 which is cylindrical instead of spherical.

A tibial part 12 is also provided, having a cylindrical external bearing surface 14 on which lies the coaxial bearing surface 10 of the meniscus element 6. As will be explained, when the knee joint is flexed, the meniscus element 6 moves along the cylindrical bearing surface 14, and to limit this movement abutments 16 and 18 are advantageously provided on the tibial part 12. The tibial part 12 is affixed to a tibial plate 20. Tibial part 12 and tibial plate 20 can also be made integral with one another. On the bottom of the tibial plate 20, cylindrical projections 22 are provided with cutting tips 24 which permit reliable anchoring in the bone, by means of screws, not shown, which are indicated only by broken lines 26.

The broken line 25 indicates that in some cases the tibial part 12 may be a separate component which is disposed in a corresponding recess in the tibial plate 20 and is secured therein. A self-locking tapered bore 27 is provided inside tubular projection 22 for a screw fastener 29. The screw fastener 29 is secured by locking means against loosening in the tibial plate 20 and can, if necessary, be unlocked again to remove the tibial plate 20 from the tibia. It may be desirable to provide threads in the projections for threaded bolts to secure the screws against loosening.

Figure 2:
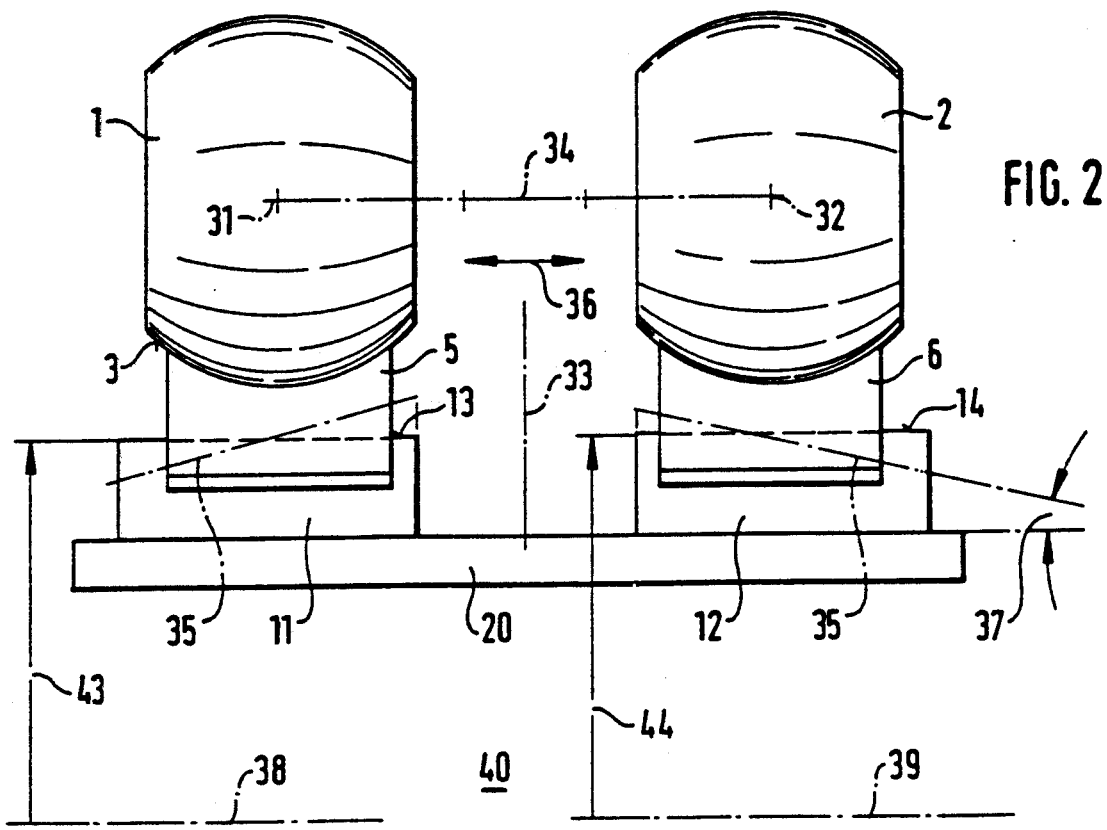
FIG. 2 is a schematic anterior view.

FIG. 2 is a ventral view of a knee-joint endoprosthesis comprising two femoral parts 1 and 2 corresponding to the natural condyles. In conjunction with FIG. 1, the spherical configuration of the bearing surfaces of the two femoral parts 1 and 2 can easily be seen with the two center points 31 and 32 and the spherical bearing surfaces 3 and 4. The radii of the femoral parts 1 and 2 are advantageously made equal. It is fundamentally possible, nevertheless, to give the two radii different lengths. It is assumed in this case that the line 34 connecting the two centers 31 and 32 is parallel to the cylinder axes 38 and 39 of the bearing surfaces of the tibial parts 11 and 12. The cylinder axes 38 and 39 lie in a common plane 40. When the endoprosthesis is in the extended state, the centers 31 and 32 also are advantageously located in the same common plane 40. This reliably assures that rotation about the vertical axis perpendicular to the tibial plate 20 will be blocked when the endoprosthesis is in the extended state. Within the scope of this invention, the cylinder axes 38 and 39 can furthermore be disposed in different planes having a given angle to one another. Also, in alternative embodiments the centers 31 and 32 and/or their connecting line 34 can be disposed outside of the common plane 40 so as to permit blocking with respect to the above-mentioned vertical axis and/or release for rotation like a natural knee joint, in accordance with requirements. Furthermore, any desired overextension is allowed in this manner.

Due to the cylindrical configuration of the tibial parts 11 and 12 and of the corresponding bearing surfaces of the two meniscus elements, movements parallel to the cylinder axis can be made as indicated by the double arrow 36. Furthermore, this assures equalization in the case of operationally required changes in the spacing between the two centers 31 and 32. Even at varied spacings, due to the transverse movability and otherwise unchanged arrangement of the tibial plate and the two tibial parts, a broad-surface contact is assured between the bearing surfaces which correspond to one another, and line contact and the resultant high pressures per unit area are avoided. The cylindrical bearing surfaces 13 and 14 of the tibial parts 11 and 12 have the radii 43 and 44 with respect to the axes of rotation 38 and 39 in the area of the tibia, and the concave bearing surfaces of the two meniscus elements 5 and 6 are made complementary thereto. Although the cylinder radii 43 and 44 are desirably equal, these cylinder radii 43 and 44 can differ in length in an alternative embodiment not shown here.

As indicated by the broken lines 35, the cylindrical bearing surfaces and cylinder axes of the tibial parts 11 and 12 can be arranged at an angle 37 to the tibial plate 20. The cylinder axes thus slope downwardly from the vertical tibial axis 33. The slope or angle of inclination can be different for each of the two tibial bearing surfaces. Also, the two tibial bearing surfaces can have opposite inclinations. Due to the aforedescribed unilateral or bilateral tilt of the bearing surfaces with respect to the tibial plate 20, important improvements in the guidance function and biological adaptation depending on requirements can be achieved. In all embodiments, the femoral parts, the meniscus elements and the tibial parts lie with their corresponding bearing surfaces in large-area contact with one another. The meniscus elements advantageously are composed of the same material as the femoral and tibial parts. The materials which have been successful in implantation, especially ceramic, can be used both for the meniscus elements and for the femoral and tibial parts.

Figure 3:
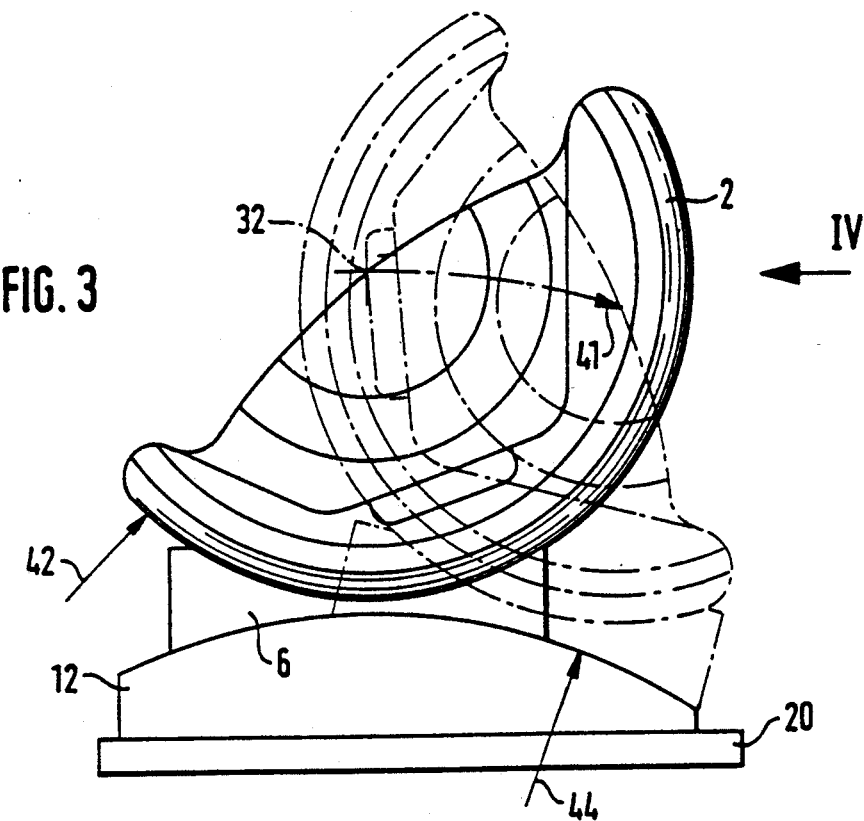
FIG. 3 is an enlarged view corresponding to FIG. 1, depicting flexion and extension.

FIG. 3 shows the femoral part 2 with a 5-degree overextension in solid lines. In contrast, the flexed position of the femoral part and the meniscus element 6 is indicated in broken lines. When the endoprosthesis is flexed, the center point 32 travels a curved path corresponding to line 41. The sphere radius 42 of the femoral part 2 advantageously lies in the range from 25 to 40 mm, while the cylinder radius 44 of the tibial part 12 can be selected in the range between 40 and 60 mm. It is important that the cylinder radius 44 be greater by a given factor than the sphere radius 42. This factor is in the range between 1.1 and 2.5, preferably between 1.2 and 2.0. The femoral part 2 extends over an angular range of about 180 degrees and has a stepped contour in its interior.

Figure 4:
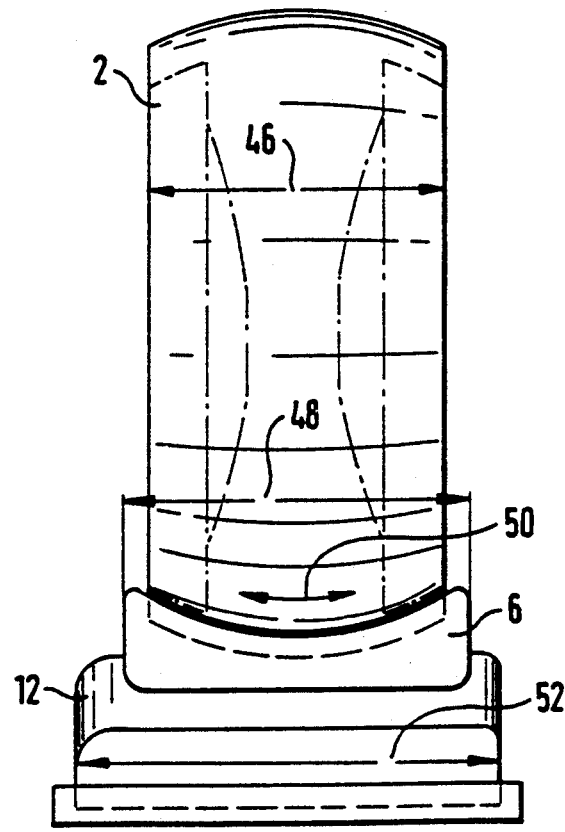
FIG. 4 is a view seen in the direction of line IV—IV in FIG. 3.

In FIG. 4, the stepped internal shape of the femoral part 2 is shown in broken lines. This results in savings in material and weight, while achieving a stable construction and also the possibility of reliable anchoring in the femur. The width 46 of the femoral part 2 is less than the width 48 of the meniscus element 6. This difference in width is chosen so that, at the maximum permissible movements indicated by the double arrow 50, the bearing surface 4 of the femoral part 2 will be fully supported in the concentric bearing surface of the meniscus element. The width 52 of the tibial part 12 is, in turn, greater than the width 48 of the meniscus element 6 so as to permit the transverse movements described above. It is apparent that transitions between different surface portions should be rounded off so as to avoid sharp edges.

Figure 5:
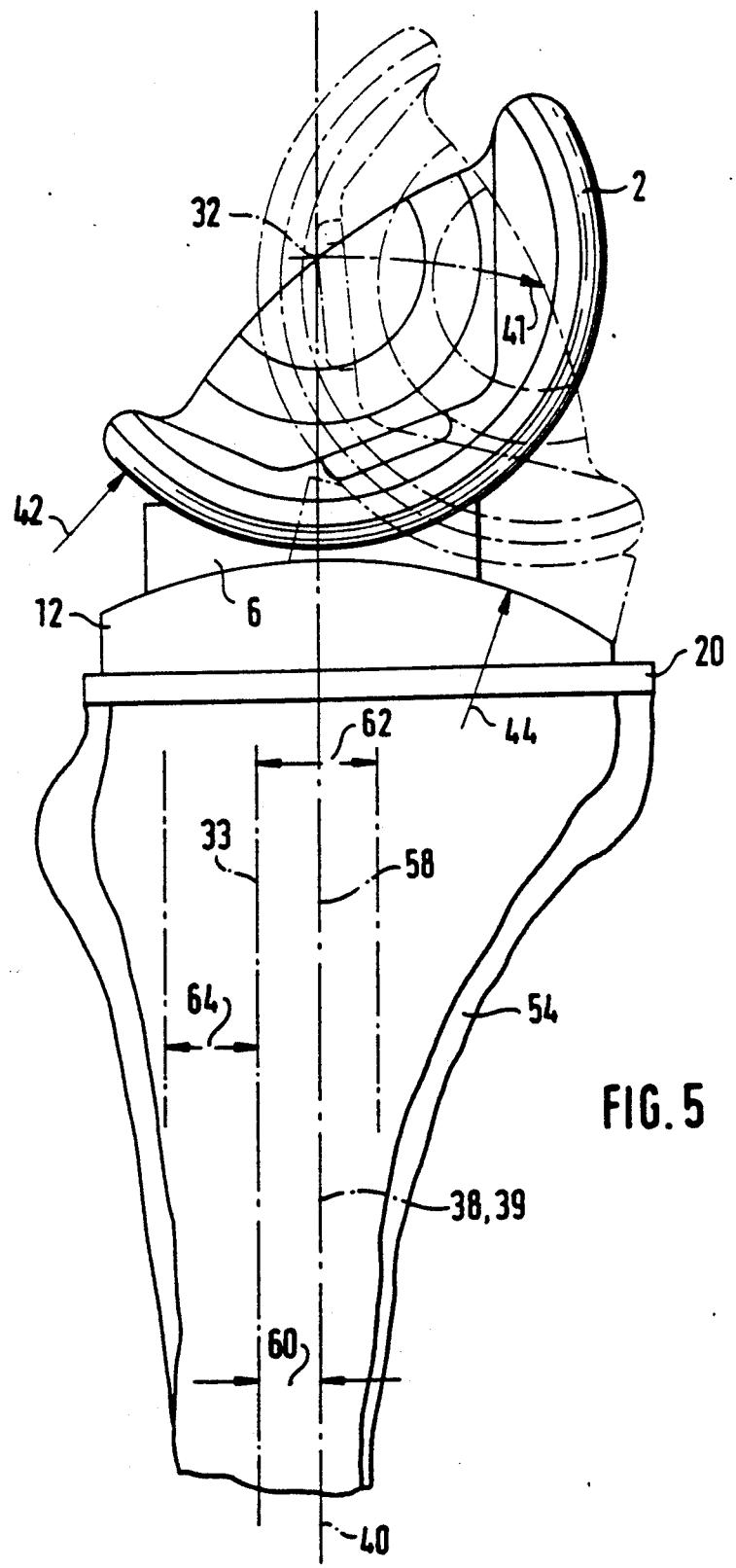
FIG. 5 is a view corresponding to FIG. 3 which illustrates the position of the cylinder axis.

In FIG. 5 the tibia 54 with the vertical axis 33 is also indicated diagrammatically. The cylinder axis 38 of the tibia part 12 does not lie on the tibial axis 33 but is shifted toward the dorsal side by an amount 60. This interval 60 is selected within a range 62 depending on the requirements of the situation, and this range can amount to as much as 10 mm. In some cases the cylinder axis 38 can also be shifted from the tibial axis 33 toward the ventral side within a range 64. In the particular embodiment shown here, at a 5-degree overextension the center point 32 of the femoral bearing surface, like the cylinder axis 38, is located on the same vertical axis which is parallel to and spaced a distance 60 from the tibial axis 33.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

What is claimed is:

1. A knee-joint endoprosthesis comprising a femoral part (2), a meniscus element (8) and a tibial part (12), wherein the femoral part (2) and the tibial part (12) have bearing surfaces which contact associated bearing surfaces (8, 10) on the meniscus element (6); the bearing surface (4) of the femoral part (2) has a spherical configuration and lies in contact with a spherically concave bearing surface (8) of the meniscus element (6); the bearing surface (14) of the tibial part (12) has a convex cylindrical configuration and lies in contact with a coaxial, cylindrically concave bearing surface (10) of the meniscus element (6), whereby the meniscus element (6) is positively guided on the cylindrical bearing surface (14) and secured against rotation relative to the tibial part about an axis extending radially of the cylindrical tibial bearing surface and through the center (32) of the femoral part (2).

2. A knee-joint endoprosthesis according to claim 1, wherein the meniscus element (6) is movable relative to the cylindrical bearing surface (14) of the tibial part (12) in three modes: 1) rotationally, 2) axially, and 3) rotationally and axially in combination, so that the meniscus element (6) is rotatable about the cylinder axis (39) as well as displaceable in translation parallel to the said cylinder axis.

3. A knee-joint endoprosthesis according to claim 1, wherein said tibial part comprises two cylindrical tibial bearing surfaces disposed spaced a distance apart on a tibial plate (20).

4. A knee-joint endoprosthesis according to claim 3, wherein said tibial bearing surfaces (13, 14) have equal radii.

5. A knee-joint endoprosthesis according to claim 3, wherein said tibial cylindrical bearing surfaces (13, 14) have radii (43, 44) which are from 40 to 60 mm long.

6. A knee-joint endoprosthesis according to claim 3, wherein said femoral part comprises two spherical bearing surfaces and the cylinder axes (38, 39) of the tibial bearing surfaces (11, 12) are disposed substantially in the same plane (40), and when the femoral part is in an extended position with respect to the tibial part (11, 12), a line (34) connecting the center points (31, 32) of the spheres defining the spherical bearing surfaces is substantially parallel to said cylinder axes.

7. A knee-joint endoprosthesis according to claim 6, wherein said center points (31, 32) are arranged to lie substantially in the same plane (40) as said cylinder axes (38, 39).

8. A knee-joint endoprosthesis according to claim 3, wherein tubular projections (22) are provided on the tibial plate (20) on its side facing away from the tibial parts (11, 12), and conically self-locking bores for screw fasteners are provided in said tubular projections.

9. A knee-joint endoprosthesis according to claim 3, wherein said bearing surfaces (11, 12) each have a cylinder axis which is inclined at an angle (37) with respect to said tibial plate (20) so that the cylinder axes slope downwardly with respect to a vertical axis (33) of the tibial part.

10. A knee-joint endoprosthesis according to claim 9, wherein each cylinder axis of the tibial part (11, 12) is shifted dorsally or ventrally a distance (60) of up to 10 mm from said vertical axis (33) of the tibial part.

11. A knee-joint endoprosthesis according to claim 1, wherein said meniscus element (5, 6) is formed of a material which has substantially the same hardness as the femoral part (1, 2) and the tibial part (11, 12).

12. A knee-joint endoprosthesis according to claim 11, wherein said meniscus element (5, 6) is formed of the same material as the femoral part (1, 2) and the tibial part (11, 12).

13. A knee-joint endoprosthesis according to claim 1, wherein the bearing surface (11, 12) of said tibial part has a cylindrical configuration, the bearing surface (7, 8) of said femoral part has a spherical configuration, and the radius (44) of said tibial bearing surface is greater than the radius (42) of said femoral part bearing surface by a factor ranging from 1.1 to 2.5.

14. A knee-joint endoprosthesis according to claim 13, wherein said cylindrically configured tibial bearing surface has a radius which is greater than the radius of the spherical femoral bearing surface by a factor ranging from 1.2 to 2.0.

15. A knee-joint endoprosthesis according to claim 1, wherein the tibial part (11, 12) has at least one end of the tibial bearing surface (14) a portion (16, 18) for limiting movement of the meniscus element (5, 6).

* * * * *